United States Patent [19]

Henley

[11] Patent Number: 5,753,468

[45] Date of Patent: May 19, 1998

[54] STABLE HIGH VISCOSITY STARCH BASED ADHESIVE AND METHOD OF PREPARATION

[75] Inventor: Matthew J. Henley, Greenwood, Ind.

[73] Assignee: National Starch and Chemical Investment Holding Corporation, Wilmington, Del.

[21] Appl. No.: 693,920

[22] Filed: Aug. 5, 1996

[51] Int. Cl.[6] .................. C12P 19/22; C12P 19/14; C12Q 1/40; C08B 31/00

[52] U.S. Cl. .................. 435/95; 435/99; 435/22; 536/102; 536/2; 536/124; 536/123.1; 536/123.13; 131/37; 106/206.1

[58] Field of Search .................. 536/102, 111, 536/112, 2, 124, 123.1, 123.13; 106/213, 206.1; 131/37; 435/99, 95, 22

[56] References Cited

U.S. PATENT DOCUMENTS

| | | | |
|---|---|---|---|
| 3,450,549 | 6/1969 | Schwalbe | 106/210 |
| 4,780,149 | 10/1988 | Kapen et al. | 127/38 |
| 4,921,795 | 5/1990 | Bozich | 435/96 |
| 4,977,252 | 12/1990 | Chiu | 536/102 |
| 5,085,228 | 2/1992 | Mooney et al. | 131/37 |
| 5,329,004 | 7/1994 | Eden et al. | 536/109 |

*Primary Examiner*—Louise Leary
*Attorney, Agent, or Firm*—Eugene Zagarella, Jr.

[57] ABSTRACT

ABSTRACT OF THE DISCLOSURE A stable starch based adhesive with good adhesive properties at low solids and high viscosity is prepared by a two-step process wherein starch is first converted using acid or alpha-amylase followed by further conversion with beta-amylase.

16 Claims, No Drawings

5,753,468

STABLE HIGH VISCOSITY STARCH BASED ADHESIVE AND METHOD OF PREPARATION

BACKGROUND OF THE INVENTION

This invention involves a process for preparing a starch based adhesive product that has excellent tackiness, drying and adhesive properties at relatively low solids and is stable and will not thicken upon long-term storage. The adhesive is prepared by a two-step process wherein the starch is first converted using acid or alpha-amylase followed by further conversion with beta-amylase Starch based adhesives are commonly used in industry. They are usually formed from native or unmodified starches, thin-boiling or converted starches or from pyrodextrinized starches. These starch based adhesives are usually used in low-solids, high viscosity systems where long-term viscosity stability is not a major factor or in high-solids, low viscosity systems (i.e., converted or dextrinized starches) where the starch has been converted to such a degree that stability has been achieved but requires high solids or low viscosity to achieve the desired adhesive properties. While these adhesives are useful in certain applications, they do not provide all the desired properties (e.g., tack, adhesion, bond strength and stability) at the usage levels defined by the adhesives of this invention.

There have been recent disclosures of high viscosity, low-solids starch based adhesives made by chemically modifying a thinned starch base. These starches are prepared by chemical and thermal means and while they have adequate adhesive properties they also posses the undesirable properties of dark color and furfural contamination which are undesirable to certain adhesive users.

U.S. Pat.3,450,549 issued Jun. 17, 1969 to H. Schwalbe relates to the production of a high-solids adhesive by subjecting starch to hydrolysis with alpha-amylase followed by thermal shearing to provide stability.

U.S. Pat. 4,921,795 issued May 1, 1990 to F. Bozich is directed to an improvement in the production of high solids dextrin adhesives wherein starch is hydrolyzed using a combination of alpha-amylase and glucoamylase.

U.S. Pat. 5,085,228 issued Feb. 4, 1992 to N. Mooney et al. is directed to an adhesive for use in cigarette manufacture which has excellent flow characteristics and viscosity stability. The adhesive is comprised of a mixture of crosslinked starch and a fluidity starch having an amylopectin content of at least 70% and is prepared by cooking at high temperature and pressure.

U.S. Pat. 5,329,004 issued Jul. 12, 1994 to J. Eden et al. discloses a liquid starch phosphate adhesive composition comprising a selected phosphorylated starch material prepared by steam injection cooking at high temperature and pressure.

U.S. Pat. 4,977,252 issued Dec. 11, 1990 to C. Chiu describes a method for producing a modified starch emulsifier characterized by shelf stability wherein the starch is derivatized with a hydrophobic moiety and is degraded with beta-amylase.

The adhesive of this invention does not require chemical derivatization or high pressure cooking to provide desired functional properties.

SUMMARY OF THE INVENTION

This invention relates to a stable starch based adhesive which has good adhesive properties at low solids and high viscosity and is prepared by a two-step process wherein starch is first converted using acid or alpha-amylase followed by further conversion with beta-amylase.

More particularly, this invention is directed to a process for preparing a stable, high viscosity starch based adhesive comprising:

a) converting a starch having an amylopectin content of 90% or more with alpha-amylase or acid to a fluidity of from about 20 to 70 WF, and b) further converting the starch with beta-amylase to provide a stable starch product having a solids of about 20 to 45% and a Brookfield viscosity of about 1000 to 5000 cPs at 22.5° C.

DETAILED DESCRIPTION OF THE INVENTION

The starch adhesive of this invention has high viscosity and is stable while providing desirable functional properties of tackiness, drying, adhesion and bond strength at relatively low solids. This adhesive product is prepared by first converting the starch with acid or alpha-amylase to a suitable viscosity level and then further converting the starch with beta-amylase to reduce the viscosity to the final desired level and also stabilize it. Adhesives with these characteristics are particularly useful in cigarette packaging, as a side-seam or tipping adhesive in cigarette manufacture and as a paperboard laminating adhesive.

The base starch starting material used in this invention is a starch having an amylopectin content of 90% or more by weight, preferably about 95% or more. Starches of this type include the waxy starches such as waxy maize, waxy rice and waxy sorghum. While the base starch may be modified to provide further desired properties, it is preferred to use non-modified starch and more preferably non-modified waxy starch.

In preparing the starch adhesive of this invention the starting starch material is first converted using alpha-amylase or acid to provide a workable, high viscosity base. These suitably converted starches have a fluidity or WF (water fluidity) of about 20 to 70 and preferably about 40 to 60. The measurement of "water fluidity" as described herein is made using a Thomas Rotational Shear-Type Viscometer (manufactured by Arthur H. Thomas Co., Philadelphia, Pa.) in accordance with standard procedures such as disclosed in U.S. Pat. No. 4,499,116 issued Feb. 12, 1985 to Zwiercan et al. Preparation of converted starches follows known techniques using alpha-amylase or treatment with acid. Alpha-amylase treatment will usually be carried out at a temperature of about 30 to 90° C., preferably about 60 to 80° C. and a pH of about 3.5 to 8.5, preferably about 4.5 to 7.5. The conditions and the terms of treatment may vary depending on the particular enzyme used and the desired degree of conversion as well as other variables such as the temperature, the type and concentration of starch, etc. The acid treatment will usually be carried out by adding mineral acid such as hydrochloric or sulfuric acid at a temperature of about 15 to 70° C., preferably about 40° to 60° C. The conditions and time of acid treatment may vary depending on the desired degree of conversion as well as other variables such as the type and concentration of mineral acid, the temperature, and the type and concentration of starch.

The starch must be cooked or gelatinized prior to treatment with enzyme, i.e., either alpha-amylase or beta-amylase. When the initial conversion is carried out by acid treatment, the starch may optionally be cooked prior to or after the acid treatment but prior to the further treatment with beta-amylase. The starch may be cooked using any of the known techniques including atmosphere cooking and jet cooking or steam injection cooking. Typical cooking temperatures can range from a temperature of at least the gelatinization temperature of the starch and can range from about 55° to 170° C. or higher depending on the conditions and type of cooking being utilized.

The initially converted starch is further converted using a beta-amylase enzyme until the starch has a Brookfield viscosity of from about 1000 to 5000 cPs at 22.5° C. and a solids of about 20 to 45%, preferably about 30 to 35%. Preferably the viscosity will be about 1500 to 3500 cPs. The beta-amylase treatment is generally carried out at a temperature of about 30° to 80° C., preferably about 50° to 70° C. and a pH of about 3.5 to 8.5, preferably about 4.5 to 7.5. The conditions and time of beta-amylase treatment can vary depending on the desired degree of conversion as well as other variables such as type of beta-amylase enzyme, temperature, type of starch, etc.

This combination of treatments unexpectedly provide an adhesive that not only is stable and has a relatively high viscosity, but also has good functional adhesive properties. As stated previously, it is known to use acid or alpha-amylase conversion of starch to provide a high viscosity, low solids system that does not have long term stability. It is also known to utilize beta-amylase to provide stable starch ingredients in food and beverage applications. However, the resulting products are high in simple sugar or maltose content and are detrimental to adhesive properties. Therefore, it is surprising that by using the combination treatment process of this invention, a stable, high viscosity starch product with good functional adhesive properties is obtained.

The following examples will further illustrate the embodiments of this invention. All percents and parts are by weight and temperatures are degrees Celsius unless otherwise indicated. The viscosities of the adhesive were determined using a Brookfield viscometer at 20 rpm and 22.5° C.

EXAMPLE 1

An acid converted starch using amioca (waxy maize) starch was prepared as follows. The starch base (1.5 kg) was slurried at 40% solids and the slurry heated to 52° C. with a constant temperature water bath. Concentrated HCI was added to the starch in the amounts noted in Table 1 and the slurry held for 16 hours. After the reaction was complete, the samples were neutralized to a pH of 4.5 using sodium carbonate, then adjusted to 5.5 with sodium hydroxide. The starch was isolated by filtration, washed and dried. The resulting converted starch had viscosities shown in Table 1.

TABLE 1

| Sample | % Acid | Water Fluidity (WF) |
|--------|--------|---------------------|
| A | 0.35 | 26 |
| B | 0.5 | 40 |
| C | 1.0 | 58 |
| D | 1.5 | 66 |
| E | 2.0 | 71 |

EXAMPLE 2

An acid converted starch using amioca (waxy maize) starch was prepared as in Example I and had a water fluidity (WF) of 50. This converted starch (1 kg) was slurried at 40% solids and the pH adjusted to 6.5 with 3% NaOH. The slurry was cooked at 149° C., 50 psi back pressure using a lab jet-cooker (Model C-1-195). After cooking, the sample was placed into a constant temperature bath set to 60° C. and 0.1% Spezyme BBA 1500 (Genecor Enzymes Inc.) brand beta-amylase added. The enzyme conversion was tracked by the viscosity which was measured at 35% solids at 22.5° C. using a Brookfield viscometer. When the viscosity reached 2700 cPs, the reaction was stopped by lowering the pH to 2.9 to 3.0 using HCI. After 30 minutes the starch based adhesive was neutralized to pH of 6.0 with NaOH. The sample was evaluated for adhesive and stability properties using the following test procedures with the results given in Table 2.

Test Method A. Viscosity Stability.

The stability of the starch was evaluated by monitoring the viscosity of the starch after the starch had been subjected to freezing and thawing. A freeze/thaw cycle accelerates unstable characteristics (i.e., retrogradation) allowing a rapid determination of stability to be evaluated. A sample of starch adhesive was cooled to −29° C. for 16 hours, then warmed slowly to 23° C. (this constitutes one freeze/thaw cycle). The viscosity of the starch was monitored before and after each freeze/thaw cycle. If there was an increase in the viscosity of the adhesive or if the adhesive gels it was rated UNSTABLE. If the viscosity remained the same through repeated cycles then the adhesive was rated STABLE.

Test Method B. Adhesive Properties.

Adhesive properties were evaluated by determining the setting speed and open time of the adhesive on cigarette tipping paper. Setting speed is defined as the time it takes an adhesive to form a fiber tearing bond. Open time is the amount of time an adhesive film remains open (or unbonded) on a substrate and still forms a durable bond when combined with a second substrate. For the evaluation of adhesive properties for this application, the set time and open time for each sample material was determined and compared to the results of an industry standard. The adhesive properties were considered satisfactory if they compared favorably or were similar to those of the standard for both tests. For example, the set speed of test sample 2A (viscosity 3500 cPs) was found to be 62 to 64 seconds and the open time was 230 to 240 seconds, both of which were similar to the properties of a comparison standard.

Similar samples were prepared using the acid converted bases produced in Example I (i.e., base starches identified by A, B, C etc.) and the method described above. Table 2 gives the properties of these adhesives. An additional commercially available acid converted base having a viscosity of 85 WF was also prepared as in this example for comparative purposes and identified as sample 2F in Table 2.

TABLE 2

| Sample | Viscosity (cPs) | Adhesive | Stable |
|--------|-----------------|----------|--------|
| 2 | 2700 | Yes | Yes |
| 2A | 3000 | Yes | Yes |
| 2A | 3500 | Yes | Yes |
| 2A | 4300 | Yes | Yes |
| 2B | 2200 | Yes | Yes |
| 2B | 2900 | Yes | Yes |
| 2C | 1800 | Yes | Yes |
| 2C | 2900 | Yes | Yes |
| 2D | 2900 | Yes | Yes |
| 2E | 2700 | Yes | No |
| 2F | 3000 | Yes | No |

EXAMPLE 3

An adhesive starch converted first by alpha-amylase and then with beta-amylase was prepared as follows: Amioca (waxy maize) starch (3 kg) was slurried at 40% solids and the pH adjusted to 6.5 with NaOH. Liquid alpha-amylase (0.0016% BAN 120L —NOVO-Nordisk, Danbury, Conn.) was added to the slurry. The slurry was then heated by steam injection to 80° C. and held at the temperature. When the cooked starch viscosity reached 14,000 cPs, the enzyme was deactivated by lowering the pH of the starch to 2.9. The pH was adjusted to 6.5 after 0.5 hours and the starch cooled to 60° C. Beta-amylase, i.e., 0.1% Spezyme was added and the reaction monitored by viscosity. When the viscosity reached 3500 cPs or other desired level, the enzyme was deactivated using acid. The adhesive viscosity and performance was tested as in Example 2 with the results given in Table 3.

Additional adhesives were also made using the above procedure with the properties and results given in Table 3.

TABLE 3

| Sample | Viscosity (cPs) (alpha-amylase) | Viscosity (cPs) (beta-amylase) | Adhesive | Stable |
| --- | --- | --- | --- | --- |
| 3 | 14,000 | 3,500 | Yes | Yes |
| 3A | 12,000 | 3,000 | Yes | Yes |
| 3B | 10,000 | 2,900 | Yes | Yes |
| 3C | 20,000 | 1,500 | Yes | Yes |

EXAMPLE 4

An adhesive was prepared for comparative purposes from unconverted amioca (waxy maize) starch. Using 1 kg of starch, a slurry was formed at 28% solids and the pH adjusted to 6.5 with NaOH. The slurry was cooked at 160° C. 80 psi back pressure using a lab jet cooker (Model C-1-1 95). After cooking, the sample was placed in a constant temperature bath set to 60° C. and 0.6% Spezyme brand beta-amylase was added. The enzyme conversion was tracked by viscosity. During conversion the starch concentrated by evaporation. The viscosity was measured at 35% solids at 22.5° C. using a Brookfield viscometer. When the viscosity reached 2,000 cPs or a desired level, the reaction was stopped by lowering the pH to 2.9 to 3.0 using HCl. After 30 minutes, the starch based adhesive was neutralized to 6.0 with NaOH. The sample was evaluated for its adhesive and stability properties as in Example 2, the product was found to have excellent stability but inferior adhesive properties.

What is claimed is:

1. A process for preparing a stable, high viscosity starch based adhesive comprising:
   a) converting a starch having an amylopectin content of 90% or more with alpha-amylase or acid to a water fluidity (WF) of from about 20 to 70 WF, and
   b) further converting the starch with beta-amylase to provide a stable starch product having a solids of about 20 to 45% and a Brookfield viscosity of about 1000 to 5000 cPs at 22.5° C.

2. The process of claim 1 wherein the base starch has an amylopectin content of 95% or more.

3. The process of claim 2 wherein the alpha-amylase or acid converted starch has a WF of from about 40 to 60.

4. The process of claim 2 wherein the beta-amylase converted starch has a Brookfield viscosity of about 1500 to 3500 cPs.

5. The process of claim 2 wherein the starch product has a solids of bout 30 to 35%.

6. The process of claim 1 wherein the starch is gelatinized prior to conversion with either alpha-amylase or beta-amylase.

7. The process of claim 1 wherein the starch base is a waxy starch.

8. The process of claim 7 wherein the alpha-amylase starch has a WF of from about 40 to 60.

9. The process of claim 7 wherein the beta-amylase converted starch has a Brookfield viscosity of about 1500 to 3500 cPs.

10. The process of claim 9 wherein the starch product has a solids of about 30 to 35%.

11. The process of claim 8 wherein the beta-amylase converted starch has a Brookfield viscosity of about 1500 to 3500 cPs.

12. The process of claim 11 wherein the starch is gelatinized prior to conversion with either alpha-amylase or beta-amylase.

13. The process of claim 12 wherein the starch product has a solids of about 30 to 35%.

14. A starch adhesive product prepared by the method of claim 1.

15. A starch adhesive product prepared by the method of claim 11.

16. A starch adhesive product prepared by the method of claim 13.

* * * * *